United States Patent
Kusagaya et al.

(10) Patent No.: US 6,414,186 B1
(45) Date of Patent: Jul. 2, 2002

(54) PROCESS FOR PRODUCING CHLOROMETHYLPHENYLACETIC ACID

(75) Inventors: Kimitoshi Kusagaya, deceased, late of Shimizu, by Mitsue Nakamura, legal representative; Yoshihiro Takao, Shizuoka; Motoaki Nakagawa, Shizuoka-ken; Masafumi Matsuzawa, Urayasu, all of (JP)

(73) Assignee: Ihara Chemical Industry Co., Ltd., Tokyo (JP)

( * ) Notice: Subject to any disclaimer, the term of this patent is extended or adjusted under 35 U.S.C. 154(b) by 0 days.

(21) Appl. No.: 09/673,797

(22) PCT Filed: Apr. 21, 1999

(86) PCT No.: PCT/JP99/02125

§ 371 (c)(1),
(2), (4) Date: Dec. 18, 2000

(87) PCT Pub. No.: WO99/54275

PCT Pub. Date: Oct. 28, 1999

(30) Foreign Application Priority Data

Apr. 22, 1998 (JP) ............................................ 10-112031

(51) Int. Cl.$^7$ ................................................ C07C 63/00
(52) U.S. Cl. ........................ 562/405; 562/493; 562/496
(58) Field of Search ................................ 562/405, 493, 562/496

(56) References Cited

U.S. PATENT DOCUMENTS 4,499,300 A  *  2/1985  Malloy et al.

FOREIGN PATENT DOCUMENTS

JP  62129250   6/1987
WO  WO-9748692  * 12/1997

* cited by examiner

Primary Examiner—Gary Geist
Assistant Examiner—Héctor M Reyes
(74) Attorney, Agent, or Firm—Birch, Stewart, Kolasch & Birch, LLP

(57) ABSTRACT

A method for preparing chloromethylphenylacetic acids represented by formula (II):

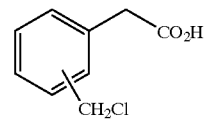

wherein a methylphenylacetic acid represented by formula (I):

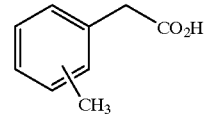

is reacted with a chlorine gas, in an inert solvent, under the irradiation with light or in the presence of a radical initiator, is disclosed. According to the preparation method, high purity chloromethylphenylacetic acids can be prepared at a high yield, without using toxic sulfuryl chloride as a chlorinating agent, by chlorinating the methyl group of the methylphenylacetic acids at a high selectivity while suppressing by-production of a dichloro form or α-chloro form.

10 Claims, No Drawings

PROCESS FOR PRODUCING CHLOROMETHYLPHENYLACETIC ACID

This application is the national phase under 35 U.S.C. §371 of PCT International Application No. PCT/JP99/02125 which has an International filing date of Apr. 21, 1999, which designated the United States of America.

TECHNICAL FIELD

The present invention relates to a method for preparing chloromethylphenylacetic acids, and more specifically to a method for preparing chloromethylphenylacetic acids at a high selectivity and a high yield, without using sulfuryl chloride as a chlorinating agent.

BACKGROUND ART

Chloromethylphenylacetic acids are compounds useful as raw materials and intermediate products for pharmaceuticals, agricultural chemicals, and the like.

One known conventional method for preparing chloromethylphenylacetic acids is a method for preparing 2-halomethylphenylacetic acids by a ring-opening reaction of 3-isochromanone with hydrogen halide, as described in the reference example of JP-A-54-138536 ("JP-A" means unexamined published Japanese patent application). However 3-isochromanone as the starting material in this method is expensive, and there is a problem in view of the production cost.

Further, a method of obtaining 2-chloromethylphenylacetic acids by reacting, in carbon tetrachloride, 2-methyl phenylacetic acid with bromine, in the presence of 2,2'-azobisisobutyronitrile (AIBN), under irradiation with ultraviolet rays, to form 2-bromomethyl phenylacetic acids, and then reacting the 2-bromomethyl phenylacetic acids with lithium chloride, is reported in *J. CHEM. SOC., CHEM. COMMUN.*, 1993, p. 399. However, this method is not preferred for industrial practice, since it involves a number of steps and the overall yield is as low as 54%.

Further, WO97/48692 reports a method of reacting 2-methyl phenylacetic acids with sulfuryl chloride, in the presence of a radical initiator, to obtain 2-chloromethylphenylacetic acid. However, the yield is 62.15% and the purity is 95.7%, with regard to the 2-chloromethylphenylacetic acids obtained by this method, which is not yet industrially satisfactory. In addition, sulfuryl chloride used in this method is toxic, and further, gaseous sulfurous acid formed by the reaction is highly toxic and corrosive, and the concentration of gaseous sulfurous acid in exhaust gases is strictly regulated, involving such problems mentioned above for industrial practice.

Accordingly, an object of the present invention is to provide a method capable of preparing chloromethylphenylacetic acids at a high yield and a high selectivity, without using sulfuryl chloride as the chlorinating agent.

Other and further objects, features, and advantages of the invention will appear more fully from the following description.

DISCLOSURE OF INVENTION

The present inventors have made earnest studies for solving the foregoing subject, and as a result, found that aimed chloromethylphenylacetic acids can be obtained at a high yield by reacting methyl phenylacetic acids and a chlorine gas, in an inert solvent, under the irradiation with light or in the presence of a radical initiator, to chlorinate only the methyl group at a high selectivity. The present inventors have accomplished the present invention based on the finding.

That is, the present invention provides:

(1) a method for preparing chloromethylphenylacetic acids represented by formula (II):

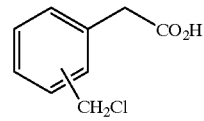

wherein a methyl phenylacetic acid represented by formula (I):

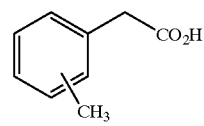

is reacted with a chlorine gas, in an inert solvent, under the irradiation with light or in the presence of a radical initiator, (2) a method for preparing chloromethylphenylacetic acids as described in (1), wherein the reaction temperature is 70° C. or lower, and (3) a method for preparing chloromethylphenylacetic acids as described in (1) or (2), wherein the inert solvent is at least one selected from monochlorobenzene, dichlorobenzenes, trichlorobenzenes, fluorobenzenes, trifluoromethylbenzenes, bistrifluoromethylbenzenes or chlorotrifluoromethylbenzenes.

BEST MODE FOR CARRYING OUT THE INVENTION

The methyl phenylacetic acid used as the starting raw material in the present invention is represented by the formula (I), and specifically one of 2-methyl phenylacetic acid, 3-methyl phenylacetic acid or 4-methyl phenylacetic acid, or a mixture of two or more of them.

The chloromethylphenylacetic acid obtained in the present invention is represented by the formula (II), and is one of 2-chloromethylphenylacetic acid, 3-chloromethylphenylacetic acid or 4-chloromethylphenylacetic acid, or a mixture of two or more of them, corresponding to the starting raw materials described above.

In the present invention, the chlorine gas is used as the chlorinating agent and the amount to be used is preferably from 0.2 to 2 mol, and more preferably from 0.8 to 1.2 mol, based on one mol of the methyl phenylacetic acid represented by the formula (I).

In the method of the present invention, the compound represented by the formula (I) and the chlorine gas are reacted under the irradiation with light or in the presence of a radical initiator. There is no particular restriction on the method of light irradiation and light including an ultraviolet region can be used preferably. For example, it can be carried out by using a mercury lamp or the like as a light source. Also for the radical initiator, those used generally can be used with no particular restriction. Specifically, benzoyl peroxide, 2,2'-azobisisobutyronitrile can be mentioned for example. The amount of the radical initiator to be used is generally from 0.005 to 0.1 mol, based on one mol of the compound represented by the formula (I).

The inert solvent usable in the present invention is a halogenated hydrocarbon, preferably, an aryl halide (for example, benzene halide), and there is no particular restriction so long as it can generally be used as the inert solvent for radial chlorinating reaction. Aryl halide includes those halogenated on the side chain. As specific examples of such inert solvent, one of monochlorobenzene, dichlorobenzenes, trichlorobenzenes, fluorobenzenes, trifluoromethylbenzenes, bistrifluoromethylbenzenes or chlorotrifluoromethylbenzenes, or a mixed solvent of two or more of them, can be used. It is, more preferably, at least one selected from monochlorobenzene, o-dichlorobenzene or 4-chlorotrifluoromethylbenzene.

There is no particular restriction on the amount of the solvent to be used in the present invention and it is preferably from 0.05 to 10 liter, and more preferably from 0.2 to 3 liter, based on one mol of the compound represented by the formula (I) in the industrial practice.

The chlorinating reaction in the present invention can be conducted at a temperature, preferably in the range of 70° C. or lower, and more preferably from 20 to 50° C.

Chloromethylphenylacetic acids at a high purity can be obtained easily at a high yield, by cooling the reaction solution after the completion of the reaction and then filtering and separating the precipitated desired compound from the reaction system. With an aim of further improving the purity, the obtained compound may be purified by recrystallization or the like.

According to the present invention, high purity chloromethylphenylacetic acids can be prepared at a high yield, without using toxic sulfuryl chlorides as a chlorinating agent, by chlorinating the methyl group of the methyl phenylacetic acids at a high selectivity while suppressing by-production of dichloro form or α-chloro form. In the method of the present invention, since reaction conditions are mild and the number of steps is reduced, it can be practiced industrially at a reduced production cost. 2-chloromethylphenylacetic acids prepared by the present invention can also be converted easily into 3-isochromanone, which is used as intermediate products for medicines and agricultural agents, by treating with a base by the known method (Zh. Org. Khim [1973] 9 (10) 2145).

EXAMPLES

Now, the present invention is described in more detail based on the following examples, which do not limit the invention.

Example 1

30 g of 2-methyl phenylacetic acid and 60 g of monochlorobenzene were charged to a 100 ml flask equipped with a gas blowing tube, a reflux condenser and a stirrer, and reaction was initiated under the irradiation with ultraviolet rays by a mercury lamp while controlling the reaction temperature to 45° C. and blowing a chlorine gas. The chlorine gas was supplied by 19 g for 8 hours.

When reaction solution after the completion of the reaction was analyzed on gas chromatography, 2-methyl phenylacetic acid as the raw material, 2-chloromethylphenylacetic acid, the desired compound, and 2-methyl-α-chlorophenylacetic acid, 2-dichloromethylphenylacetic acid, 2-chloromethyl-α-chlorophenylacetic acid as by-products were present each at the ratio shown in Table 1. The selectivity to 2-chloromethylphenylacetic acid (ratio of 2-chloromethylphenylacetic acid in the products) was 88.7%.

After the completion of the reaction, the reaction solution was cooled to 20° C., and precipitates were filtered and separated to obtain 26.6 g of 2-chloromehtyl phenylacetic acid (purity: 98.5%, yield: 72%).

Examples 2 to 4

2-chloromethylphenylacetic acid was prepared in the same manner as in Example 1 except for using the solvents shown in Table 1 instead of monochlorobenzene. When the reaction solution after the completion of the reaction was analyzed on gas chromatography, each of the compounds was present at the ratio shown in Table 1. The selectivity to 2-chloromethylphenylacetic acid is also shown in Table 1.

Examples 5 to 8

2-chloromethylphenylacetic acid was prepared in the same manner as in Example 1 except for changing the reaction temperature and/or amount of solvent as shown in Table 1. When the reaction solution after the completion of the reaction was analyzed on gas chromatography, each of the compounds was present at the ratio shown in Table 1. The selectivity to 2-chloromethylphenylacetic acid is also shown in Table 1.

Example 9

4-chloromethylphenylacetic acid was prepared in the same manner as in Example 1 except for using 30 g of 4-methyl phenylacetic acid instead of 2-methyl phenylacetic acid and using 90 g of monochlorobenzene.

When reaction solution after the completion of the reaction was analyzed on gas chromatography, 6.8% of 4-methyl phenylacetic acid as the raw material, 74.8% of 4-chloromethylphenylacetic acid, the desired compound, and 0.5% of 4-methyl-α-chlorophenylacetic acid, 5.8% of 4-dichloromethylphenylacetic acid and 7.7% of 4-chloromethyl-α-chlorophenylacetic acid, as by-products, were present. The selectivity to 4-chloromethylphenylacetic acid was 80.2%.

After the completion of the reaction, the reaction solution was cooled to 20° C., and precipitates were filtered and separated to obtain 26.2 g of 4-chloromehtyl phenylacetic acid (purity: 96.4%, yield: 71%).

Comparative Example 1

30 g of 2-methyl phenylacetic acid, 60 g of monochlorobenzene and 2,2'-azobisisobutyronitrile as a radical initiator were charged to a 200 ml flask equipped with a reflux condenser, a stirrer and a thermometer, and the reaction temperature was controlled to 70° C. and 29.7 g of sulfuryl chloride was added dropwise thereto for 5 hours.

When the reaction solution after the completion of the reaction was analyzed on gas chromatography, each of the compounds was present at the ratio shown in Table 1. The selectivity to 2-chloromethylphenylacetic acid was 75.4%.

After the completion of the reaction, the reaction solution was cooled to 20° C., and precipitates were filtered and separated to obtain 23.0 g of 2-chloromehtyl phenylacetic acid (purity: 96.8%, yield: 62%).

Reference Example 1

2-chloromethylphenylacetic acid was prepared in the same manner as in Example 1 except for changing the reaction temperature to 80° C. When the reaction solution after the completion of the reaction was analyzed on gas chromatography, each of the compounds was present at the ratio shown in Table 1. The selectivity to 2-chloromethylphenylacetic acid was 70.0%.

TABLE 1

|  | No. | Solvent | Amount of solvent (g) | Chrolinating agent | Reaction temperature (° C.) | GC composition (area %) | | | | | Selectivity*6 (%) |
|---|---|---|---|---|---|---|---|---|---|---|---|
|  |  |  |  |  |  | OMPA*1 | 2CMPA*2 | α-Cl OMPA*3 | 2DCMPA*4 | α-Cl CMPA*5 |  |
| Example | 1 | monochlorobenzene | 60 | chlorine gas | 45 | 4.5 | 84.7 | 1.4 | 3.9 | 4.4 | 88.7 |
|  | 2 | o-dichlorobenzene | 75 | chlorine gas | 45 | 5.0 | 81.6 | 1.5 | 5.2 | 5.4 | 85.9 |
|  | 3 | 1,3-bistrifluoro methylbenzene | 60 | chlorine gas | 45 | 19.8 | 70.7 | 0.9 | 2.0 | 3.8 | 88.1 |
|  | 4 | 4-chlorotrifluoro methylbenzene | 120 | chlorine gas | 45 | 5.7 | 81.9 | 1.0 | 4.3 | 5.5 | 86.8 |
|  | 5 | monochlorobenzene | 60 | chlorine gas | 60 | 8.5 | 75.4 | 2.6 | 7.0 | 5.8 | 82.4 |
|  | 6 | monochlorobenzene | 240 | chlorine gas | 20 | 5.2 | 83.1 | 1.6 | 4.5 | 3.6 | 87.7 |
|  | 7 | monochlorobenzene | 60 | chlorine gas | 20 | 6.7 | 84.5 | 0.1 | 3.4 | 4.2 | 90.6 |
|  | 8 | monochlorobenzene | 60 | chlorine gas | 5 | 3.0 | 86.7 | 0.2 | 2.1 | 3.7 | 89.4 |
| Comparative Example | 1*7 | monochlorobenzene | 60 | sulfuryl chloride | 70 | 6.6 | 70.4 | 2.5 | 11.3 | 8.8 | 75.4 |
| Reference Example | 1 | monochlorobenzene | 60 | chlorine gas | 80 | 2.2 | 68.5 | 1.7 | 12.0 | 9.4 | 70.0 |

(note)
*1OMPA: 2-methylphenylacetic acid
*2 2CMPA: 2-chloromethylphenylacetic acid
*3 α-ClOMPA: 2-methyl-α-chlorophenylacetic acid
*4 2DCMPA: 2-dichloromethylphenylacetic acid
*5 α-ClCMPA: 2-chloromethyl-α-chlorophenylacetic acid
*6Selectivity (ratio of 2CMPA in product) (%) = 100 × [2CMPA/(100 − OMPA)]
*7 2,2'-azobisisonitrile was used instead of mercury lamp irradiation

INDUSTRIAL APPLICABILITY

The preparation method according to the present invention is suitable as a method for preparing high purity chloromethylphenylacetic acids at a high yield, without using toxic sulfuryl chloride as a chlorinating agent, by chlorinating the methyl group of methyl phenylacetic acid at a high selectivity while suppressing by-production of dichloro form or α-chloro form. The method of the present invention can be practiced industrially at a reduced production cost since the reaction conditions are mild and the number of steps is reduced. Further, 2-chloromethylphenylacetic acid prepared by the method of the present invention can also be converted easily into 3-isochromanone by treating with a base by a known method, which can be used as intermediate products for medicines and agricultural chemicals.

Having described our invention as related to the present embodiments, it is our intention that the invention not be limited by any of the details of the description, unless otherwise specified, but rather be construed broadly within its spirit and scope as set out in the accompanying claims.

What is claimed is:

1. A method for preparing chloromethylphenylacetic acids represented by formula (II):

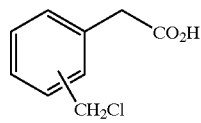

wherein a methylphenylacetic acid represented by formula (I):

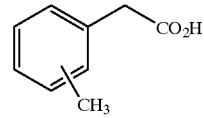

is reacted with a chlorine gas, in an inert solvent, under the irradiation with light or in the presence of a radical initiator.

2. The method for preparing chloromethylphenylacetic acids as claimed in claim 1, wherein the reaction temperature is 70° C. or lower.

3. The method for preparing chloromethylphenylacetic acids as claimed in claim 2, wherein the reaction temperature is in a range of from 20 to 50° C.

4. The method for preparing chloromethylphenylacetic acids as claimed in claim 1, wherein the inert solvent is at least one selected from monochlorobenzene, dichlorobenzenes, trichlorobenzenes, fluorobenzenes, trifluoromethylbenzenes, bistrifluoromethylbenzenes or chlorotrifluoromethylbenzenes.

5. The method for preparing chloromethylphenylacetic acids as claimed in claim 4, wherein the inert solvent is at least one selected from monochlorobenzene, o-dichlorobenzene or 4-chlorotrifluoromethylbenzene.

6. The method for preparing chloromethylphenylacetic acids as claimed in claim 1, wherein from 0.2 to 2 mol of the chlorine gas is reacted with one mol of methylphenylacetic acids represented by the formula (I).

7. The method for preparing chloromethylphenylacetic acids as claimed in claim 1, wherein the reaction is carried out under the irradiation with light and the light irradiation is conducted with light including an ultraviolet region.

8. The method for preparing chloromethylphenylacetic acids as claimed in claim 1, wherein the reaction is carried out in the presence of the radical initiator and the radical initiator is benzoyl peroxide or 2,2'-azobisisobutyronitrile.

9. The method for preparing chloromethylphenylacetic acids as claimed in claim 1, wherein the reaction is carried out in the presence of a radical initiator and the amount of the radical initiator to be used is from 0.005 to 0.1 mol based on one mol of the compound represented by the formula (I).

10. The method for preparing chloromethylphenylacetic acids as claimed in claim 1, wherein from 0.05 to 10 liter of the inert solvent is used based on one mol of the compound represented by the formula (I).

* * * * *